(12) United States Patent
Shiotani et al.

(10) Patent No.: US 8,927,504 B2
(45) Date of Patent: Jan. 6, 2015

(54) COMBINED USE OF DIPEPTIDYL PEPTIDASE 4 INHIBITOR AND SWEETENER

(75) Inventors: Masaharu Shiotani, Osaka (JP); Tomomi Ishihara, Osaka (JP); Chiaki Matsushita, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 302 days.

(21) Appl. No.: 12/594,568

(22) PCT Filed: Apr. 3, 2008

(86) PCT No.: PCT/JP2008/056678
§ 371 (c)(1),
(2), (4) Date: Oct. 2, 2009

(87) PCT Pub. No.: WO2008/120813
PCT Pub. Date: Oct. 9, 2008

(65) Prior Publication Data
US 2010/0113382 A1    May 6, 2010

Related U.S. Application Data

(60) Provisional application No. 60/907,471, filed on Apr. 3, 2007.

(30) Foreign Application Priority Data

Apr. 3, 2007   (JP) ................................. 2007-097079

(51) Int. Cl.
| | | |
|---|---|---|
| A61K 31/70 | (2006.01) | |
| A61K 31/54 | (2006.01) | |
| A61K 31/047 | (2006.01) | |
| A61K 31/7016 | (2006.01) | |
| A61K 31/702 | (2006.01) | |
| A61P 3/04 | (2006.01) | |
| A61K 45/06 | (2006.01) | |
| A61K 31/40 | (2006.01) | |
| A61K 31/496 | (2006.01) | |
| A61K 31/7004 | (2006.01) | |

(52) U.S. Cl.
CPC ............... A61K 45/06 (2013.01); A61K 31/047 (2013.01); A61K 31/40 (2013.01); A61K 31/496 (2013.01); A61K 31/54 (2013.01); A61K 31/7004 (2013.01); A61K 31/702 (2013.01)
USPC ............. 514/23; 514/53; 514/61; 514/222.5; 514/738

(58) Field of Classification Search
USPC ............................. 514/23, 53, 61, 222.5, 738
See application file for complete search history.

(56) References Cited

U.S. PATENT DOCUMENTS

| 6,710,040 B1 * | 3/2004 | Hulin et al. ............... 514/210.17 |
| 6,777,397 B2 * | 8/2004 | Zehner et al. .................... 514/53 |
| 7,138,397 B2 * | 11/2006 | Yasuda et al. ............. 514/254.01 |
| 2004/0087514 A1 | 5/2004 | Hughes et al. |
| 2005/0065145 A1 * | 3/2005 | Cao et al. .................... 514/222.5 |

FOREIGN PATENT DOCUMENTS

| EP | 1520486 A1 * | 4/2005 | .............. A23L 1/308 |
| JP | 10-290681 | 11/1998 | |
| JP | 2007-001946 | 1/2007 | |
| WO | WO-2005/020920 A2 | 3/2005 | |
| WO | WO-2005/036990 A1 | 4/2005 | |

OTHER PUBLICATIONS

The Merck Manual, 1992, 16th Ed., p. 981.*
Aschner, P., et al., "Effects of the Dipeptidyl Peptidase-4 Inhibitor Sitagliptin as Monotherapy on Glycemic Control in Patients With Type 2 Diabetes," Diabetes Care, vol. 29, No. 12, pp. 2632-2637 (2006).
Charbonnel, B., et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone," Diabetes Care, vol. 29, No. 12, pp. 2638-2643 (2006).
Gee, J. M., et al., "Dietary Lactitol Fermentation Increases Circulating Peptide YY and Glucagon-Like Peptide-1 in Rats and Humans," Nutrition, vol. 21, pp. 1036-1043 (2005).
Supplementary European Search Report for EP 08 73 9785, dated Mar. 8, 2012.

* cited by examiner

*Primary Examiner* — Ganapathy Krishnan
(74) *Attorney, Agent, or Firm* — Finnegan, Henderson, Farabow, Garrett & Dunner, L.L.P.

(57) ABSTRACT

The present invention provides a novel therapeutic or preventive method, a pharmaceutical composition and use thereof, that exhibit superior anti-obesity effects (body weight-reducing (losing) effects and/or body fat mass-reducing effects). Specifically, the present invention provides a pharmaceutical composition comprising the combination of a dipeptidyl peptidase 4 inhibitor and a sweetener having a GLP-1 secretion-stimulating action, as well as use thereof for the manufacture of a medicament. The present invention also provides a method for treating or preventing obesity, comprising administering an effective amount of (a) a dipeptidyl peptidase 4 inhibitor and (b) a sweetener having a GLP-1 secretion-stimulating action to a patient suffering from symptoms of obesity.

8 Claims, 5 Drawing Sheets

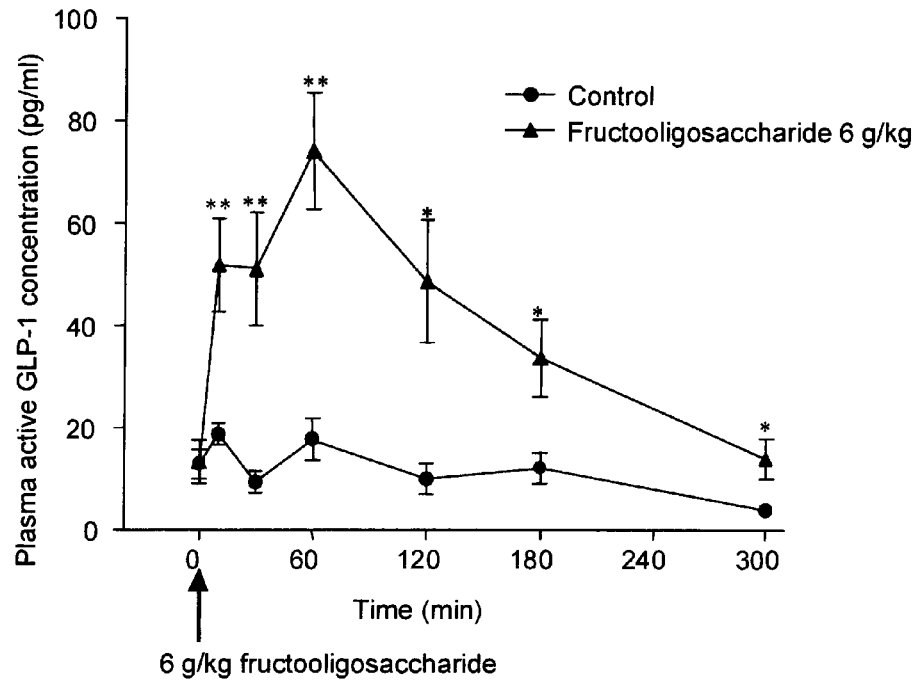
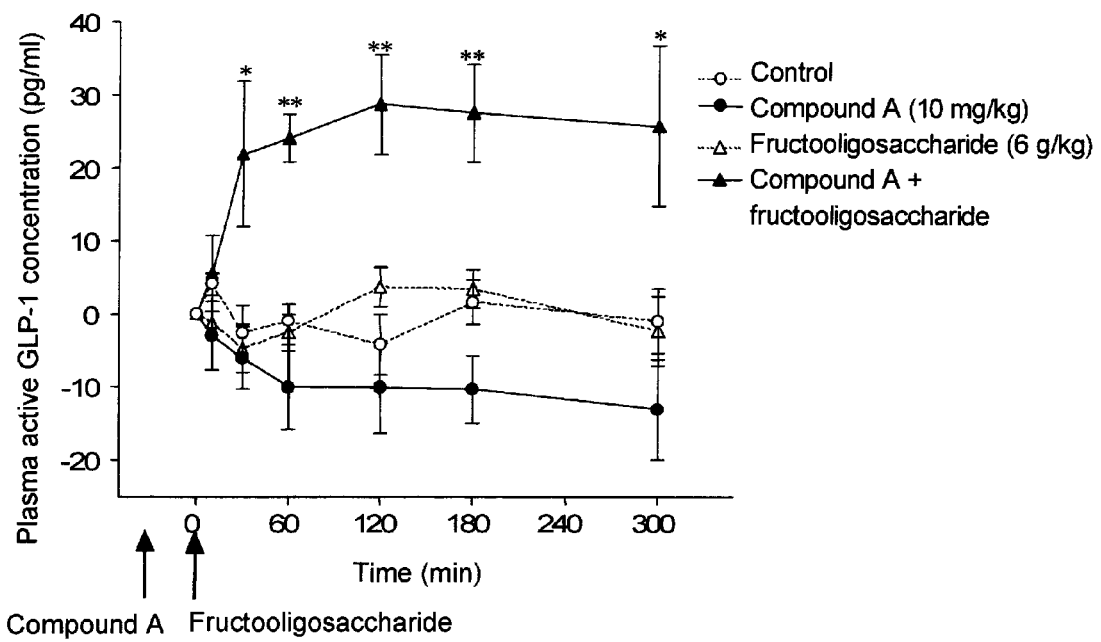

COMBINED USE OF DIPEPTIDYL PEPTIDASE 4 INHIBITOR AND SWEETENER

CROSS REFERENCE TO RELATED APPLICATIONS

This application is a national phase application based on PCT/JP2008/056678, filed Apr. 3, 2008, which claims the priority of Japanese Application No. 2007-097079, filed Apr. 3, 2007, and claims the benefit of U.S. Provisional Application No. 60/907,471, filed Apr. 3, 2007, the content of all of which is incorporated herein by reference in their entirety.

TECHNICAL FIELD

The present invention relates to a method for reducing body weight, reducing body fat mass and/or treating or preventing obesity, a pharmaceutical composition for the same, and use thereof.

More specifically, the present invention relates to a method for reducing body weight, reducing body fat mass and/or treating or preventing obesity, a pharmaceutical composition and use thereof, which comprise combined use of (1) a dipeptidyl peptidase 4 inhibitor, and (2) a sweetener having a GLP-1 secretion-stimulating action.

BACKGROUND ART

Although obesity is becoming a serious social problem in modern society, the effects of existing obesity therapeutic drugs (such as Orlistat, Dexfenfluramine, Sibutramine or Phentermine) are not always adequate while also having problems relating to adverse side effects.

Obesity causes numerous health problems either by itself or in correlation with other diseases. Examples of life-threatening diseases associated with obesity include hypertension, type 2 diabetes, hyperinsulinemia, insulin resistance, dyslipidemia, hyperlipidemia, arteriosclerosis and heart disease.

Among these, there is an intimate relationship between type 2 diabetes and obesity.

Examples of causative factors of type 2 diabetes include impaired pancreatic insulin secretion and insulin resistance. Hypertrophy of fat tissue in obesity not only decreases the number of insulin receptors of fat cells, but also accelerates the secretion of insulin resistance-inducing cytokines such as TNF-α from fat cells, thereby causing insulin resistance.

Thus, prevention of obesity is important for type 2 diabetes patients and persons at risk thereto, and alleviation of obesity is strongly required in type 2 diabetes patients with obesity in combination.

On the other hand, dipeptidyl peptidase 4 (DPP4) is a type of serine protease that specifically hydrolyzes a dipeptide of Xaa-Pro or Xaa-Ala (wherein Xaa may be any amino acid) from the N terminal of a polypeptide chain.

GLP-1 (glucagon-like peptide 1) is a peptide hormone that mainly has the augmented action in glucose-stimulated insulin secretion, is primarily secreted from the lower small intestine after meals, and acts in the pancreas. DPP4 deactivates this GLP-1 by hydrolyzing it, as well as DPP4 causes the production of peptides that act as antagonists of GLP-1 receptors.

Compounds that inhibit the enzyme activity of DPP4 (DPP4 inhibitors) enhance glucose-stimulated insulin secretion by enhancing the action of intrinsic GLP-1 by means of this inhibitory action, thereby demonstrating blood sugar lowering action, while improving impaired glucose tolerance.

Consequently, DPP4 inhibitors are considered to be useful in the prevention and treatment of such diseases as diabetes, and numerous DPP4 inhibitors have been developed as therapeutic drugs for diabetes (in particular type 2 diabetes) (Augustyns, et al., Expert Opin. Ther. Patents, 2003, 13: 499-510; Campbell, Ann. Pharmacother., 2007, 41:51-60).

Analogues of GLP-1 have also been developed as therapeutic drugs for diabetes. In addition, there are also reports suggesting that GLP-1 has an anorexic action. For analogues of GLP-1, reports have been observed indicating that anti-obesity effects have been obtained in clinical studies in humans (Zander, et al., Lancet, 2002, 359:824-830; Iltz, J. L., et al., Clin. Ther., 2006, 28(5):652-65; Mack, et al., Int. J. Obes., 2006, 30(9):1332-40; DeFronzo, et al., Diabetes Care, 2005, 28(5):1092-100).

Although DPP4 inhibitors are expected to demonstrate effects in the treatment or prevention of obesity and the like, there has been no preclinical or clinical reports so far indicating that significant anti-obesity effects were obtained by administration of DPP4 inhibitors alone.

The following is known with respect to saccharides.

Various saccharides are known to cause a rise in GLP-1 levels. In addition, several saccharides are known to inhibit weight gain by administration thereof.

For example, a publication by Shima, et al. (Acta Endocrinologica, 1990, 123:464-470) discloses that blood GLP-1 levels are increased following administration of saccharides such as D-glucose, D-galactose, maltose, sucrose or maltitol.

A publication by Tokunaga, et al. (J. Nutri. Sci. Vitaminol., 1986, 32:111-121) and Japanese Examined Patent Publication No. S62-60369 disclose that inhibition of weight gain is observed by administration of fructooligosaccharide to rats.

Publications by Cani, et al. disclose that administration of oligofructose (Raftilose; mixture of glucosyl-(fructosyl) n-fructose and (fructosyl) m-fructose; average degree of polymerization: 4.5) to rats or mice increases GLP-1 concentration in blood and intestine, decreases blood sugar levels during glucose loading, and demonstrates effects on reducing body weight in high fat diet-fed rats etc. (Cani, et al., British Journal of Nutrition, 2004, 92:521-526; Cani, et al., Obesity, 2005, 13:1000-1007; Cani, et al. Journal of Endocrinology, 2005, 185:457-465; Cani, et al., Diabetes, 2006, 55:1484-1490; and WO 2005/36990).

Japanese Unexamined Patent Publication No. H6-65080 discloses a health food for preventing obesity that contains L-arabinose, D-xylose and the like, and that administration of L-arabinose inhibited weight gain in mice.

Japanese Unexamined Patent Publication No. H10-290681 discloses an anti-obesity agent and/or body fat mass reducing agent and the like having a xylooligosaccharide as an active ingredient thereof.

However, the combined use of a DPP4 inhibitor with a sweetener such as a saccharide for the purpose of anti-obesity effects is not known.

Patent Document 1: Japanese Examined Patent Publication No. S62-60369

Patent Document 2: Japanese Unexamined Patent Publication No. H6-65080

Patent Document 3: Japanese Unexamined Patent Publication No. H10-290681

Patent Document 4: International Patent Publication No. WO2005/36990

Non-Patent Document 1: Augustyns, et al., Expert Opin. Ther. Patents, 2003, 13: 499-510

Non-Patent Document 2: Campbell, Ann. Pharmacother., 2007, 41:51-60

Non-Patent Document 3: Zander, et al., Lancet, 2002, 359: 824-830

Non-Patent Document 4: Iltz, J. L., et al., Clin. Ther., 2006, 28(5):652-65

Non-Patent Document 5: Mack, et al., Int. J. Obes., 2006, 30(9):1332-40

Non-Patent Document 6: DeFronzo, et al., Diabetes Care, 2005, 28(5):1092-100

Non-Patent Document 7: Shima, et al., Acta Endocrinologica, 1990, 123:464-470

Non-Patent Document 8: Tokunaga, et al., J. Nutri. Sci. Vitaminol., 1986, 32:111-121

Non-Patent Document 9: Cani, et al., British Journal of Nutrition, 2004, 92:521-526

Non-Patent Document 10: Cani, et al., Obesity, 2005, 13:1000-1007

Non-Patent Document 11: Cani, et al. Journal of Endocrinology, 2005, 185:457-465

Non-Patent Document 12: Cani, et al., Diabetes, 2006, 55:1484-1490

DISCLOSURE OF THE INVENTION

Problems to be Solved by the Invention

The present invention provides a novel therapeutic or preventive method, a pharmaceutical composition and use thereof, that exhibit superior anti-obesity effects (body weight-reducing (losing) effects and/or body fat mass-reducing effects).

The present invention also provides a method, a pharmaceutical composition and use thereof, that exhibit, in addition to the aforementioned superior effects, therapeutic or preventive effects against diabetes (such as blood sugar lowering effects).

Means for Solving the Problems

As a result of conducting extensive studies, the inventors of the present invention found that by using a sweetener having an action in stimulating intrinsic GLP-1 secretion in combination with a DPP4 inhibitor, superior anti-obesity effects (body weight-reducing (losing) effects and/or body fat mass-reducing effects) are obtained, thereby leading to completion of the present invention.

Namely, the present invention is a pharmaceutical composition comprising the combination of a dipeptidyl peptidase 4 inhibitor and a sweetener having a GLP-1-secretion-stimulating action.

The present invention is also a pharmaceutical composition comprising a dipeptidyl peptidase 4 inhibitor, which is for combined use with a sweetener having a GLP-1 secretion-stimulating action.

Also, the present invention is a method for treating or preventing obesity comprising administering an effective amount of (a) a dipeptidyl peptidase 4 inhibitor and (b) a sweetener having a GLP-1 secretion-stimulating action to a patient suffering from symptoms of obesity. In an embodiment of the present invention, administration of (a) can be carried out any of simultaneous to, before or after administration of (b).

Moreover, the present invention includes the use of a combination comprising a dipeptidyl peptidase 4 inhibitor and a sweetener having a GLP-1 secretion-stimulating action for the manufacture of a medicament.

In addition, the present invention includes a packaged product, comprising as active ingredients a dipeptidyl peptidase 4 inhibitor and a sweetener having a GLP-1 secretion-stimulating action, together with instructions for simultaneous, separate or continuous use for treating or preventing obesity.

EFFECTS OF THE INVENTION

According to the pharmaceutical composition, therapeutic or preventive method, and use thereof according to the present invention, superior anti-obesity effects (body weight-reducing effects and/or body fat mass-reducing effects) are obtained in a patient suffering from symptoms of obesity.

In addition, according to the present invention, therapeutic or preventive effects against diabetes (such as blood sugar lowering effects) can be simultaneously obtained in addition to the aforementioned superior effects. Thus, the pharmaceutical composition, therapeutic or preventive method, and use thereof according to the present invention is particularly useful for patients suffering from symptoms of obesity together with symptoms of diabetes (in particular type 2 diabetes).

BRIEF DESCRIPTION OF THE DRAWINGS

FIG. 1 shows the test results for action in increasing plasma active GLP-1 level in the case of having administered fructooligosaccharide to DPP4-deficient rats (F344/DuCrlCrlj). Black triangles (▲) indicate time-dependent changes in plasma active GLP-1 concentration (mean±standard error (SEM)) in a group orally administered 6 g/kg of fructooligosaccharide, while black circles (●) indicate the same time-dependent changes in a control group administered purified water (n=6 for both groups). (*: $p<0.05$, **: $p<0.01$: significant difference versus control group based on Dunnett's multiple comparison method.)

FIG. 2 shows the test results for action in increasing plasma active GLP-1 level in the case of having administered DPP4 inhibitor (Compound A) and fructooligosaccharide to C57BL/6J mice. White circles (○) indicate time-dependent changes in plasma active GLP-1 concentration (mean±standard error (SEM)) in a control group administered purified water only, black circles (●) indicate the same time-dependent changes in a group orally administered 10 mg/kg of DPP4 inhibitor (Compound A) alone, white triangles (Δ) indicate the same time-dependent changes in a group orally administered 6 g/kg of fructooligosaccharide alone, and black triangles (A) indicate the same time-dependent changes in a group orally administered 10 mg/kg of DPP4 inhibitor (Compound A) and 6 g/kg of fructooligosaccharide (n=5 for all groups). (*: $p<0.05$, **: $p<0.01$: significant differences versus control group based on Dunnett's multiple comparison method.)

BEST MODE FOR CARRYING OUT THE INVENTION

Figure 3:
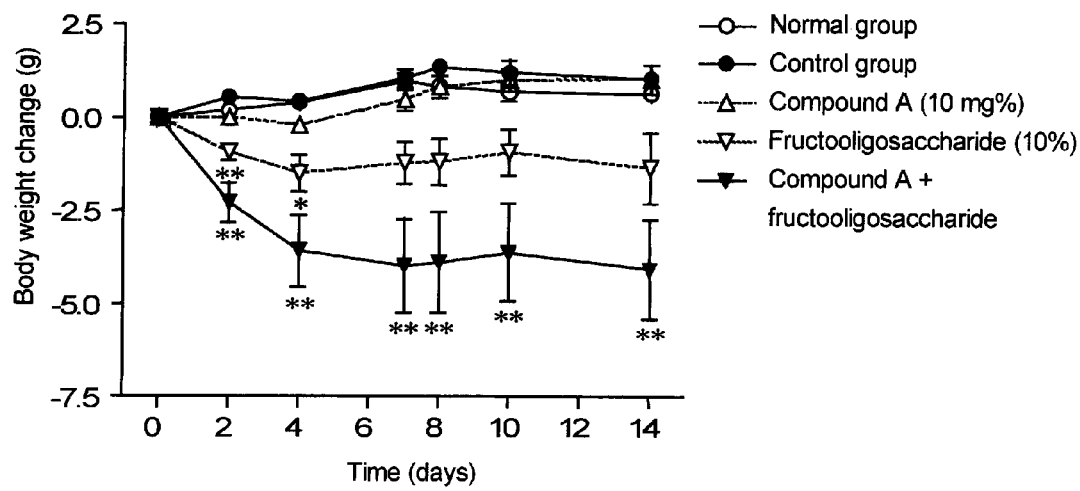
FIG. 3 shows the test results for action in reducing body weight in the case of in-feed administration of DPP4 inhibitor (Compound A) and fructooligosaccharide to high fat diet-fed C57BL/6J mice. White circles (○) indicate daily changes in body weight (mean±standard error (SEM)) in a group of normal mice not fed a high fat diet, black circles (●) indicate the same daily changes in a group fed only a high fat diet as a control, white triangles (Δ) indicate the same daily changes in a group of high fat diet-fed mice administered in-feed 10 mg/100 g of DPP4 inhibitor (Compound A) alone, inverted white triangles (∇) indicate the same daily changes in a group of high fat diet-fed mice administered in-feed 10 w/w % of fructooligosaccharide alone, and inverted black triangles (▼) indicate the same daily changes in a group of high fat diet-fed mice administered in-feed both 10 mg/100 g of DPP4 inhibitor (Compound A) and 10 w/w % of fructooligosaccharide (n=9 to 10 for all groups). (*: $p<0.05$, **: $p<0.01$: significant differences versus control group based on Dunnett's multiple comparison method.)

In the present invention, a compound having the ability to inhibit the enzyme activity of dipeptidyl peptidase 4 by acting directly thereon is usually used as a dipeptidyl peptidase 4 inhibitor. This compound may be peptide-like or non-peptide-like, and a non-peptide-like compound is preferable. Examples of the forms of inhibition include competitive inhibition, non-competitive inhibition, uncompetitive inhibition or a mixed inhibition thereof.

Dipeptidyl peptidase 4 inhibitors are widely known, and various such compounds are disclosed in the following publications, for example. The compounds disclosed in these publications can be suitably used for the dipeptidyl peptidase 4 inhibitor used in the present invention, but it is not limited thereto.

Tanabe Seiyaku WO2002/30891 and its corresponding U.S. Pat. No. 6,849,622;

Tanabe Seiyaku WO2002/30890 and its corresponding U.S. Pat. No. 7,138,397;

Ferring WO1995/15309, WO2001/40180, WO2001/81304, WO2001/81337, WO2003/00250, WO2003/35057;

Probiodrug AG WO1997/40832, EP1082314, WO1999/61431, WO2003/015775;

Novartis WO1998/19998, WO2000/34241, WO2001/96295, U.S. Pat. No. 6,107,317, U.S. Pat. No. 6,110,949, U.S. Pat. No. 6,172,081;

GSK WO2003/002531, WO2003/002530, WO2003/002553;

BMS WO2001/68603, WO2002/83128, WO2005/012249;

Merck WO2002/76450, WO2003/004498;

Syrrx WO2005/026148, WO2005/030751, WO2005/095381, WO2004/087053, WO2004/103993;

Mitsubishi Welpharma WO2002/14271, U.S. Pat. No. 7,060,722, U.S. Pat. No. 7,074,794, WO2003/24942, Japanese Unexamined Patent Publication No. 2002-265439, Japanese Unexamined Patent Publication No. 2005-170792, WO2006/88129;

Taisho Seiyaku WO2004/020407;

Yamanouchi Seiyaku WO2004/009544;

Kyowa Hakko WO2002/051836;

Kyorin Seiyaku WO2005/075421, WO2005/077900, WO2005/082847;

Alantos WO2006/116157;

Glenmark WO2006/090244, WO2005/075426;

Sanwa Kagaku Kenkyusho WO2004/067509; and,

LG Lifescience WO2005/037828, WO2006/104356.

An example of a preferable dipeptidyl peptidase 4 inhibitor is a compound represented by the following general formula [Ia], or pharmaceutically acceptable salt thereof, disclosed in U.S. Pat. No. 6,849,622:

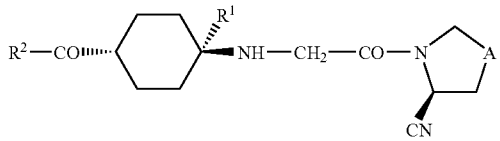

[Ia]

wherein,

A represents —$CH_2$— or —S—, $R^1$ represents a hydrogen atom, a lower alkyl, a hydroxy lower alkyl or a lower alkoxy lower alkyl, and $R^2$ represents (1) a cyclic group which may be substituted, where the cyclic group portion is (i) a monocyclic, bicyclic or tricyclic hydrocarbon group or (ii) a monocyclic, bicyclic or tricyclic heterocyclic group, or (2) an amino group which may be substituted.

Specific examples of these include:

(2S)-2-cyano-1-[trans-4-(dimethylaminocarbonyl)cyclohexylamino]acetylpyrrolidine;

(2S)-2-cyano-1-[trans-4-(morpholinocarbonyl)cyclohexylamino]acetylpyrrolidine;

(2S)-2-cyano-1-[trans-4-(4-acetylpiperazin-1-yl-carbonyl)cyclohexylamino]acetylpyrrolidine; etc., and pharmaceutically acceptable salts thereof In addition, another example of a preferable dipeptidyl peptidase 4 inhibitor is a compound represented by general formula [Ib], or a pharmaceutically acceptable salt thereof, disclosed in U.S. Pat. No. 7,138,397:

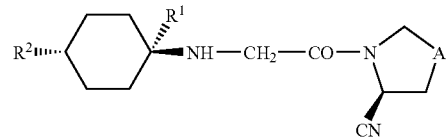

[Ib]

wherein,

A represents —$CH_2$—, $R^1$ represents H, a lower alkyl, a hydroxy lower alkyl or a lower alkoxy lower alkyl, and $R^2$ represents a piperazinyl group which may be substituted.

Specific examples of these include:

(2S)-2-cyano-1-[t-4-(4-acetyl-1-piperazinyl)-1-methyl-r-1-cyclohexylamino]acetylpyrrolidine; and (2S)-2-cyano-1-[t-4-(4-propionyl-1-piperazinyl)-1-methyl-r-1-cyclohexylamino]acetylpyrrolidine; etc., and pharmaceutically acceptable salts thereof.

In addition, another example of a preferable dipeptidyl peptidase 4 inhibitor is an L-proline derivative represented by the following general formula, or pharmaceutically acceptable salt thereof, disclosed in U.S. Pat. No. 7,074,794:

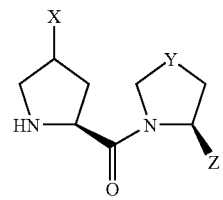

wherein,

X represents —$NR^1R^2$ (wherein, $R^1$ and $R^2$ may be the same or different and each is independently cycloalkylalkyl, arylalkyl, heteroaryl or heteroarylalkyl, or may be bonded to each other to form a heterocycle optionally containing 1 or 2 nitrogen atoms or oxygen atoms, the heterocycle optionally being condensed with an aromatic ring optionally having substituents, and the heterocycle optionally being a spiro ring);

—$NR^3COR^4$ (wherein, $R^3$ and $R^4$ are the same or different and each is independently a hydrogen atom, alkyl, cycloalkyl, cycloalkylalkyl, aryl, arylalkyl, arylalkenyl, heteroaryl or heteroarylalkyl);

—$NR^5CONR^6R^7$ or —$NR^5CH_2CH_2NR^6R^7$ (wherein, $R^5$, $R^6$ and $R^7$ are the same or different and each is independently hydrogen atom, alkyl, acyl, cycloalkyl, cycloalkylalkyl, aryl, arylalkyl, heteroaryl or heteroarylalkyl, or $R^6$ and $R^7$ may be bonded to each other to form a heterocycle optionally containing 1 or 2 nitrogen atoms or oxygen atoms, the heterocycle optionally being condensed with an aromatic ring optionally having substituents);

—$NR^8SO_2R^9$ (wherein, $R^8$ and $R^9$ are the same or different and each is independently a hydrogen atom, alkyl, cycloalkyl, cycloalkylalkyl, aryl, arylalkyl, heteroaryl or heteroarylalkyl); or, —$OR^{10}$ or —$OCOR^{11}$ (wherein, $R^{10}$ and $R^{11}$ are each a hydrogen atom, alkyl, cycloalkyl, cycloalkylalkyl, aryl, arylalkyl, heteroaryl or heteroarylalkyl); and, Y represents CH$_2$, CH—OH, S, S=O or SO$_2$;

Z represents a hydrogen atom or a cyano;

and, of the above-mentioned groups, alkyl, aryl, arylalkyl, arylalkenyl, heteroaryl, heteroarylalkyl, cycloalkyl, cycloalkylalkyl and heterocycle each optionally have substituted.

Specific examples of these compounds include 3-{(2S,4S)-4-[4-(3-methyl-1-phenyl-5-pyrazolyl)-1-piperazinyl]-2-pyrrolidinylcarbonyl}-1,3-thiazolidine, etc. and pharmaceutically acceptable salts thereof, and more preferably, 3-{(2S,4S)-4-[4-(3-methyl-1-phenyl-1H-pyrazol-5-yl)piperazin-1-yl]pyrrolidin-2-ylcarbonyl}thiazolidine and pharmaceutically acceptable salts thereof disclosed in WO 2006/88129.

U.S. Pat. Nos. 6,849,622, 7,138,397 and 7,074,794 and International Patent Publication No. WO2006/88129 are herein incorporated by reference.

In the previous and subsequent descriptions, examples of lower alkyl groups (or alkyl groups), lower alkylthio groups (or alkylthio groups), lower alkylsulfonyl groups (or alkylsulfonyl groups), lower alkoxy groups (or alkoxy groups) and lower alkylamino groups (or alkylamino groups) include linear or branched groups having 1 to 6 carbon atoms, in particular those having 1 to 4 carbon atoms. In addition, examples of lower alkanoyl groups (or alkanoyl groups) and lower alkanoylamino groups (or alkanoylamino groups) include linear or branched groups having 2 to 7 carbon atoms in particular 2 to 5 carbon atoms. Moreover, examples of halogen atoms include fluorine, chlorine, bromine and iodine.

In the previous and subsequent descriptions, examples of pharmaceutically acceptable salts include inorganic acid salts such as hydrochlorides, sulfates, nitrates, phosphates or hydrobromides, and organic acid salts such as acetates, fumarates, oxalates, citrates, methanesulfonates, benzenesulfonates, p-toluenesulfonates and maleates. In addition, in the case the dipeptidyl peptidase 4 inhibitor has a substituent such as a carboxyl group, examples of pharmaceutically acceptable salts include salts with bases (including alkaline metal salts such as sodium salts and potassium salts, and alkaline earth metal salts such as calcium salts).

Other preferable examples of dipeptidyl peptidase 4 inhibitors include the compounds indicated below.

Sitagliptin (development code: MK-0431, commercial name: Januvia) or an equivalent thereto, namely (3R)-3-amino-1-[9-(trifluoromethyl)-1,4,7,8-tetraazabicyclo[4.3.0]nona-6,8-dien-4-yl]-4-(2,4,5-trifluorophenyl) butan-1-one or a pharmaceutically acceptable salt thereof (such as a phosphate);

Vildagliptin (development code: LAF237, commercial name: Galvus) or an equivalent thereto, namely (2S)-1-[2-[(3-hydroxy-1-adamantyl)amino]acetyl]pyrrolidine-2-carbonitrile or a pharmaceutically acceptable salt thereof;

Saxagliptin (development code: BMS-477118) or an equivalent thereto, namely (1S,3S,5S)-2-[(2S)-2-amino-2-(3-hydroxy-1-adamantyl)acetyl]-2-azabicyclo[3.1.0]hexane-3-carbonitrile or pharmaceutically acceptable salt thereof;

Alogliptin (development code: SYR-322) or an equivalent thereto, namely 6-[(3R)-3-aminopiperidin-1-yl]-1-(2-cyanobenzyl)-3-methylpyrimidin-2,4(1H,3H)-dione] or pharmaceutically acceptable salt thereof (such as benzoate); and L-threo-isoleucyl pyrrolidide, L-allo-isoleucyl thiazolidide, L-allo-isoleucyl pyrrolidide and pharmaceutically acceptable salts thereof The sweetener used in combination with the DPP4 inhibitor in the present invention is a sweetener having a GLP-1 secretion-stimulating action.

As used herein, "a GLP-1 secretion-stimulating action" refers to an action that increases active GLP-1 levels in the blood, for example, refers to an action that increases active GLP-1 levels in the blood (such as in plasma) to higher levels in the case of having administered through the digestive tract (orally or intestinally) into the body of a human or non-human mammal in comparison to the absence of administration.

The sweetener may be a saccharide or a non-saccharide sweetener (such as an artificial sweetener).

A sweetener having a GLP-1 secretion-stimulating action is preferably those which substantially cause no increase in blood sugar levels in the case of having administered through the digestive tract (orally or intestinally) into the body of a human or non-human mammal. Glucose is undesirable since prominent increases in blood sugar levels occur as a result of administration thereof.

From this viewpoint, in the case of using a saccharide as a sweetener having a GLP-1 secretion-stimulating action, the use of a non-metabolizable and/or poorly digestible and poorly absorbable saccharide is preferable.

Examples of non-metabolizable and/or poorly digestible and poorly absorbable saccharides include saccharides composed of unit saccharides that the living body of a human or non-human mammal does not have ability to utilize thereof. Alternatively, examples of these saccharides include those having a structure that is not easily degraded by digestive enzyme groups possessed by the body of a human or non-human mammal itself [such as digestive enzymes present in the small-intestinal epithelial mucosal layer (including disaccharide hydrolases such as sucrase, glucoamylase, isomaltase or lactase)], examples of which include saccharides having linkages other than α-1,4 linkages and β-1,4 linkages, and saccharides having unit saccharides that are resistant to degradation by disaccharide hydrolases in the small intestine.

Non-saccharide sweeteners such as artificial sweeteners frequently are low in calories and normally do not cause an increase in blood sugar levels.

A more specific example of a sweetener (saccharide) having a GLP-1 secretion-stimulating action that can be used preferably is a fructooligosaccharide [namely, a mixture comprising saccharides containing structure in which 2 to 8 fructofuranosyl moieties are linked to a single α-D-glucopyranosyl moiety (such as kestose, nistose, fructofuranosyl nistose or the like)].

In addition, each of constituents of fructooligosaccharides in the form of kestose (glucose-1,2-fructose-1,2-fructose), nistose (glucose-1,2-fructose-1,2-fructose-1,2-fructose) and fructofuranosyl nistose (glucose-1,2-fructose-1,2-fructose-1,2-fructose-1,2-fructose) and the like can be used alone in substantially pure form instead of in the form of a mixture.

All of these are non-metabolizable and/or poorly digestible and poorly absorbable saccharides.

In addition, xylose (in particular its D-form) can be preferably used as a sweetener (saccharides) having a GLP-1 secretion-stimulating action.

In the present description, oligosaccharides refer to saccharides having a structure in which a plurality (normally 2 to 9 and preferably 2 to 6) of constituent monosaccharides are linked together, or mixtures thereof.

In addition to those described above, examples of other sweeteners (saccharides) having a GLP-1 secretion-stimulating action include the saccharides [oligosaccharides (such as di- to hexa-saccharides or a mixture of oligosaccharides) and sugar alcohols] indicated below.

Disaccharide, such as
Melibiose [α-D-galactopyranosyl-(1→6)-D-glucose],
Isomaltase [α-D-glucopyranosyl-(1→6)-D-glucose],
Gentiobiose [β-D-glucopyranosyl-(1→6)-D-glucose],
Trehalose [α-D-glucopyranosyl α-D-glucopyranoside],
Isotrehalose [β-D-glucopyranosyl β-D-glucopyranoside],
Neotrehalose [β-D-glucopyranosyl α-D-glucopyranoside],
Nigerose [α-D-glucopyranosyl-(1→3)-D-glucose],
Maltulose [α-D-glucopyranosyl-(1→4)-D-fructose],
Isomaltulose [α-D-glucopyranosyl-(1→6)-D-fructose],
Lactulose [β-D-galactopyranosyl-(1→4)-D-fructose],
Kojibiose [α-D-glucopyranosyl-(1→2)-D-glucose],
Sophorose [β-D-glucopyranosyl-(1→2)-D-glucose],
Laminarabio se [β-D-glucopyranosyl-(1→3)-D-glucose],
Cellobiose [β-D-glucopyranosyl-(1→4)-D-glucose],
Cellobionic acid [β-D-glucopyranosyl-(1→4)-D-gluconic acid],
Galactosucrose [β-D-fructofuranosyl α-D-galactopyranoside; Fruf(β2-1α)Ga1],
Lactosamine (LacN) [β-D-galactopyranosyl-(1→4)-D-glucosamine],
Lactosediamine [2-amino-2-deoxy-β-D-galactopyranosyl-(1→4)-D-glucosamine],
Lactobionic acid [β-D-galactopyranosyl-(1→4)-D-gluconic acid],
Neolactose [β-D-galactopyranosyl-(1→4)-D-altrose],
Primeverose [β-D-xylopyranosyl-(1→6)-D-glucose],
Rutinose [α-L-rhamnopyranosyl-(1→6)-D-glucose],
Scillabiose [β-D-glucopyranosyl-(1→4)-L-rhamnose],
Turanose [α-D-glucopyranosyl-(1→3)-D-fructose],
Vicianose [α-L-arabinopyranosyl-(1→6)-D-glucose],
Xylobiose (disaccharide in which two xylose molecules are linked via β-1,4 linkage).
Trisaccharide, such as Raffinose
[galactose-1,6-glucose-1,2-fructose;
β-D-fructofuranosyl α-D-galactopyranosyl-(1→6)-α-D-glucopyranoside], Cellotriose
[β-D-glucopyranosyl-(1→4)-β-D-glucopyranosyl-(1→4)-D-glucose], Chacotriose
[α-L-rhamnopyranosyl-(1→2)-[α-L-rhamnopyranosyl-(1→4)]-D-glucose], Gentianose
[β-D-fructofuranosyl β-D-glucopyranosyl-(1→6)-α-D-glucopyranoside], Isomaltotriose
[α-D-glucopyranosyl-(1→6)-α-D-glucopyranosyl-(1→6)-D-glucose], Isopanose
[α-D-glucopyranosyl-(1→4)-[α-D-glucopyranosyl-(1→6)]-D-glucose], Maltotriose
[α-D-glucopyranosyl-(1→4)-α-D-glucopyranosyl-(1→4)-D-glucose], Manninotriose
[α-D-galactopyranosyl-(1→6)-α-D-galactopyranosyl-(1→6)-D-glucose], Melezitose
[α-D-glucopyranosyl-(1→3)β-D-fructofuranosyl α-D-glucopyranoside], Panose
[α-D-glucopyranosyl-(1→6)-α-D-glucopyranosyl-(1→4)-D-glucose], Planteose
[α-D-galactopyranosyl-(1→6)-β-D-fructofuranosyl α-D-glucopyranoside], Solatriose
[α-L-rhamnopyranosyl-(1→2)-[β-D-glucopyranosyl-(1→3)]-D-galactose]Umbelliferose
[β-D-fructofuranosyl α-D-galactopyranosyl-(1→2)-α-D-galactopyranoside].
Tetrasaccharide, such as Stachyose
[β-D-fructofuranosyl α-D-galactopyranosyl-(1→6)-α-D-galactopyranosyl-(1→6)-α-D-glucopyranoside], Lycotetraose
[β-D-glucopyranosyl-(1→2)-[β-D-xylopyranosyl-(1→3)]-β-D-glucopyranosyl-(1→4)-β-D-galactose], Maltotetraose
[α-D-glucopyranosyl-(1→4)-α-D-glucopyranosyl-(1→4)-α-D-glucopyranosyl-(1→4)-D-glucose].
Pentasaccharide, such as Maltopentaose
[α-D-glucopyranosyl-(1→4)-α-D-glucopyranosyl-(1→4)-α-D-glucopyranosyl-(1→4)-α-D-glucopyranosyl-(1→4)-D-glucose], Verbascose
[β-D-fructofuranosyl α-D-galactopyranosyl-(1→6)-α-D-galactopyranosyl-(1→6)-α-D-galactopyranosyl-(1→6)-α-D-glucopyranoside].
Hexasaccharide, such as Maltohexaose
[α-D-glucopyranosyl-(1→4)-α-D-glucopyranosyl-(1→4)-α-D-glucopyranosyl-(1→4)-α-D-glucopyranosyl-(1→4)-α-D-glucopyranosyl-(1→4)-D-glucose].
Mixture of oligosaccharides, such as
oligotose (mixture of maltose, maltotriose and the like),
maltooligosaccharide,
isomaltooligosaccharide,
glucooligosaccharide,
beet oligosaccharide (beet extract containing raffinose),
galactooligosaccharide,
gentiooligosaccharide,
nigerooligosaccharide,
inulooligosaccharide,
lactooligosaccharide (mixture consisting mainly of lactosucrose),
soybean oligosaccharide, and
xylooligosaccharide.
Sugar alcohols, such as
threitol (in particular its D-form),
erythritol,
xylitol,
arabinitol (in particular its D-form),
ribitol,
sorbitol (also known as sorbit or glucitol),
mannitol (in particular its D-form),
allitol,
galactitol (also known as dulcitol),
iditol (in particular its D-form),
talitol (altritol) (in particular its D-form),
lactitol (β-D-galactopyranosyl-(1→4)-D-glucitol),
palatinit, and
maltitol (α-D-glucopyranosyl-(1→4)-D-glucitol).
Examples of oligosaccharides having a GLP-1 secretion-stimulating action (those are non-metabolizable and/or poorly digestible and poorly absorbable) include saccharides having a structure in which a plurality (normally 2 to 9 and preferably 2 to 6) of the same or different unit saccharides selected from the following "unit saccharide group" are linked together (with the proviso that those saccharides in which all of the unit saccharides are D-glucopyranose are excluded), or mixtures thereof. Preferable examples of these saccharides are those that contain a linkage type other than an α-1,4 glycoside linkage and β-1,4 glycoside linkage.
Unit Saccharide Group:
D-glucopyranose (glucose);
D-fructofuranose (fructose);
xylopyranose (xylose); and
D-galactopyranose (galactose).
Examples of sugar alcohols having a GLP-1 secretion-stimulating action (those are non-metabolizable and/or poorly digestible and poorly absorbable) include sugar alcohols that are the reduced forms of aldoses having 4 to 6 carbon atoms (such as D-glucose, D-mannose, D-erythrose, D-galactose, D-threose, L-threose, D-ribose, D-arabinose, D-xylose, D-allose, D-idose or D-talose, of which the D-forms thereof are preferable), or sugar alcohols that are the reduced forms of disaccharides and/or trisaccharides having aldoses of 4 to 6 carbon atoms as their unit saccharides.

Examples of non-saccharide sweeteners having a GLP-1 secretion-stimulating action that can be used include acesulfame K (acesulfame potassium), sucralose, aspartame (artificial sweetener having a dipeptide structure in which the methyl ester of a phenylalanine is linked to aspartic acid through an amide linkage) and stevia (stevioside, extract or refined product of stevia leaves).

Preferable examples of sweeteners having a GLP-1 secretion-stimulating action used in the present invention include the sweeteners of (1), (2), (3), (4) and (5) indicated below:

(1) fructooligosaccharide, kestose, nistose or fructofuranosyl nistose;

(2) xylose (in particular D-xylose);

(3) oligosaccharides such as melibiose, raffinose, isomaltose, xylobiose or xylooligosaccharide;

(4) sugar alcohols such as mannitol, sorbitol, erythritol, maltitol or xylitol; and, (5) non-saccharide sweeteners such as acesulfame K or sucralose.

More preferable examples of these sweeteners include saccharides such as melibiose, mannitol, sorbitol or erythritol, and non-saccharide sweeteners such as acesulfame K.

Further preferable examples of these sweeteners include melibiose and mannitol for saccharides, and acesulfame K for the non-saccharide sweetener.

The sweeteners (saccharides or non-saccharide sweeteners) can be used in the form of a liquid or powder.

The GLP-1 secretion stimulating actions of sweeteners having a GLP-1 secretion-stimulating action can be confirmed by a method such as that described in Experiment Example 1 or 2 described hereinafter.

Although the GLP-1 secretion stimulating action of each sweetener may be tested under conditions of administering a DPP4 inhibitor, as is described in Experiment Example 1 described hereinafter, the GLP-1 secretion stimulating action can be confirmed more easily by using a DPP4-deficient animal.

F344 rats available from Charles River Laboratories Japan, Inc. (F344/DuCrlCrlj) are known to be lacking DPP4, and are preferable for such testing.

There are no particular limitations on the form of combination use of the DPP4 inhibitor and sweetener having a GLP-1 secretion-stimulating action.

An example thereof may be a combined formulation form in which both the DPP4 inhibitor and the sweetener having a GLP-1 secretion-stimulating action are incorporated within the same preparation.

Alternatively, the DPP4 inhibitor and the sweetener having a GLP-1 secretion-stimulating action may be each incorporated in the form of separate preparations and both separate preparations may be administered simultaneously.

In addition, the DPP4 inhibitor and the sweetener having a GLP-1 secretion-stimulating action may be each in the form of separate preparations, and the separate preparations may be administered sequentially (either in this order or in the reverse order) or continuously.

In the present invention, the DPP4 inhibitor and the sweetener having a GLP-1 secretion-stimulating action can each be used with an inert carrier corresponding to the administration method, and can be used after formulating in the form of a commonly used pharmaceutical preparation. Examples of carriers include binders (such as gum arabic, gelatin, sorbit or polyvinyl pyrrolidone), excipients (such as lactose, saccharose or cornstarch), lubricants (such as magnesium stearate, talc or polyethylene glycol), and disintegrating agents (such as potato starch) for which the use thereof is acceptable in ordinary pharmaceuticals. In the case of an injection preparation or intravenous drip preparation, the DPP4 inhibitor and the sweetener having a GLP-1 secretion-stimulating action can be formulated using distilled water for injection, physiological saline or aqueous glucose solution and the like.

There are no particular limitations on the preparation form, and commonly used preparation forms can be applied, examples of which include tablets, granules, capsules, powders, solutions, suspensions, emulsions, injection preparations and intravenous drip preparations.

In addition, the preparation may also be formulated in the form of dry syrup, syrup, chewable tablets or effervescent tablets and the like. Among these preparation forms, granules, powders, dry syrups, syrups, chewable tablets and effervescent tablets are preferable.

The therapeutic or preventive method, pharmaceutical composition and use thereof according to the present invention can be applied to the treatment or prevention of obesity. The therapeutic or preventive method, pharmaceutical composition and use thereof according to the present invention can also be applied to the reduction of body weight or the reduction of body fat mass. The therapeutic or preventive method, pharmaceutical composition and use thereof according to the present invention can further be applied for reduction of body weight or reduction of body fat mass in patients suffering from symptoms of obesity. In addition, the therapeutic or preventive method, pharmaceutical composition and use thereof according to the present invention can also be applied to patients with both symptoms of type 2 diabetes and obesity. Furthermore, the therapeutic or preventive method, pharmaceutical composition and use thereof according to the present invention can be applied for reduction of body weight or reduction of body fat mass in patients suffering from symptoms of type 2 diabetes and obesity.

The pharmaceutical composition of the present invention may also contain at least one pharmaceutically acceptable carrier or excipient in addition to the dipeptidyl peptidase 4 inhibitor and the sweetener having a GLP-1 secretion-stimulating action. In addition, the pharmaceutical composition of the present invention can be in the form of a combined preparation for simultaneous, separate, sequential or continuous use.

There are no particular limitations on the administration method in the case where the pharmaceutical composition and therapeutic or preventive method of the present invention are applied to medical use, and typical oral or parenteral methods (such as intravenous, intramuscular, subcutaneous, transcutaneous, transnasal or other transmucosal or enteral) can be applied.

The dosage of the DPP4 inhibitor may be suitably set within the range of an adequate amount sufficient for demonstrating pharmacological effects corresponding to the potency and properties of the compound used for the active ingredient.

Although varying according to the administration method and age, body weight and conditions of the subject (such as a patient) to be administered, the dosage of the DPP4 inhibitor is set to a typical dosage, and is set to, for example, a suitable amount normally within the range of 0.001 to 300 mg/kg body weight per day.

The dosage of the DPP4 inhibitor may be set to an amount required for inhibiting enzyme activity of dipeptidyl peptidase 4 in the living body to be administered normally by 30% or more, preferably by 60% or more and more preferably by 90% or more at 24 hours after administration.

The dosage of the sweetener having a GLP-1 secretion-stimulating action may be suitably set within the range of an adequate amount sufficient for demonstrating pharmacological effects in combination with the DPP4 inhibitor corresponding to the potency and properties of the saccharide used.

Although varying according to the administration method and age, body weight and conditions of the subject (such as a patient) to be administered, the dosage of the sweetener having a GLP-1 secretion-stimulating action is set to, for example, a suitable amount normally within the range of 0.001 to 5.0 g/kg body weight per day.

Administration of a large dose of the sweetener having a GLP-1 secretion-stimulating action (in particular non-metabolizable and/or poorly digestible and poorly absorbable saccharides) may easily result in the occurrence of diarrhea and other gastrointestinal tract symptoms.

Thus, it is desirable to make the dose of the sweetener as small as possible, and is to administer only the amount required for demonstrating pharmacological effects as a result in combination with the DPP4 inhibitor.

From the viewpoint of avoiding gastrointestinal tract symptoms, the dosage of non-metabolizable and/or poorly digestible and poorly absorbable saccharides is normally set to within the range of 3 g/kg body weight or less, preferably 1 g/kg body weight or less and more preferably 0.3 g/kg body weight or less.

On the other hand, from the viewpoint of the need to demonstrate pharmacological effects, the dosage of the sweetener (such as mannitol or sorbitol) is preferably set to within the range of 0.01 g/kg body weight or more and more preferably to 0.03 g/kg body weight or more.

Furthermore, although saccharides such as mannitol or sorbitol may also be used as inert carriers for the purpose of formulation, the use of these saccharides as inert carriers together with the DPP4 inhibitor is not included in the present invention.

Examples of DPP4 in the present invention include human or non-human mammalian DPP4.

Examples of subjects to which medicaments, pharmaceutical compositions and therapeutic or preventive methods in the present invention are applied include humans or non-human mammals (in particular preferably humans).

Anti-obesity effects (body weight reduction effects and/or body fat mass-reducing effects) can be confirmed through in vivo testing using a known animal model.

Examples of such testing methods include methods using DIO (diet-induced obesity) mice produced by high fat diet feeding, normal rats (SD rats), and DIO (diet-induced obesity) rats produced by high fat diet feeding (Int. J. Obes., 2006, 30:1332-1340; Obesity Res., 2005, 13, 1000-1007; etc.), or equivalent methods thereto.

More specifically, testing can be carried out in the same manner as the method described in, for example, Example 3 described hereinafter.

EXAMPLES

The following provides an explanation of the present invention using examples thereof, but the present invention is not limited to these examples.

Example 1

GLP-1 Secretion-Stimulating Action of Sweetener in DPP4-Deficient Rats (F344DucrlCrlj) (Blood Active GLP-1 Level-Increasing Action)

(1) Test Method:
Male F344DucrlCrlj rats (Charles River Laboratories Japan, Inc.) (7 to 10-week-old at time of use) were used for the study animals. F344DucrlCrlj rats are known to be rats of a strain having a spontaneous DPP4 gene deficiency (Watanabe, et al., Experientia, 1987, 43:400-401).

These study animals were used in the test after fasting starting on the night prior to the test and grouping according to body weight. The animals were orally administered (10 mL/kg) a solution of the test sweetener (or purified water as a control) followed by collecting blood samples from the tip of the tail at 0, 30, 60, 180 and 360 minutes after dosing. These samples were then measured for concentrations of active GLP-1 in plasma.

Measurement of plasma active GLP-1 concentrations was carried out in the following manner. The collected blood samples were centrifuged (4° C., 3000 rpm, 10 minutes) to obtain plasma. Plasma GLP-1 concentrations were then measured using the Bio-Plex Suspension Array System (Rat Endocrine LINCOplex Kit; available from Linco Research, Inc.) or the Glucagon-like Peptide-1 (Active) ELISA Kit™ (available from Linco Research, Inc.; active GLP-1 measurement kit).

The measurement results were tested for the presence of a significant difference between groups by comparing the sweetener-loaded group with the control group using Dunnett's multiple comparison test (two-sided test). Here, a P value less than 5% was considered statistically significant, and statistical analysis software (EXSAS: Biological Experimental Data Statistical Analysis System, from Arm Systex Co., Ltd.) was used to analyze the data.

(2) Test Results:
Blood active GLP-1 level-increasing action was tested for the cases of having dosed with sweetener and the control in accordance with the method described in (1) above.

Fructooligosaccharide (Meiji Seika Kaisha Ltd.) was used for the test sweetener and administered orally at 6 g/kg/10 mL. Purified water was administered as a control. As a result, in the group dosed with fructooligosaccharide, levels of active GLP-1 in plasma demonstrated significantly higher values in comparison with the control group at each of 30, 60, 180 and 360 minutes after dosing.

The results are shown in FIG. 1.

In addition, similar tests were carried out using xylose and xylitol for the test sweeteners and administering these saccharides orally at 3 to 6 g/kg/10 mL each. As a result, the levels of active GLP-1 in plasma demonstrated remarkably high values in groups dosed with these saccharides as compared with the control group.

Example 2

GLP-1 Secretion-Stimulating Action by Combined Use of DPP4 Inhibitor and Sweetener (Blood Active GLP-1 Level-Increasing Action) (1)

(1) Test Method:
Male SD(CD)/Crj rats (Charles River Laboratories Japan, Inc.) (6-week-old at time of use) or male C57BL/6J mice (Clea Japan, Inc.) (9-week-old at time of use) were used in the test.

These study animals were used in the test after first grouping according to body weight. The animals were orally administered (10 mL/kg) a test DPP4 inhibitor (or purified water as a control). At 30 minutes after administration, the animals were then orally administered (10 mL/kg) a solution of a test sweetener (or purified water as a control) followed by collecting blood samples at 0, 30, 60, 180 and 300 minutes after administration. These samples were then measured for concentrations of active GLP-1 in plasma.

Measurement of plasma active GLP-1 concentrations was carried out in the same manner as (1) of Example 1 above.

The measurement results were tested for the presence of a significant difference between groups by comparing the sweetener-loaded groups with the control group using Dunnett's multiple comparison test (two-sided test). Here, a P value less than 5% was considered statistically significant, and statistical analysis software (EXSAS: Biological Experimental Data Statistical Analysis System, Arm Systex Co., Ltd.) was used to analyze the data.

(2) Test Results:

Blood active GLP-1 level-increasing action was tested for the case of combined use of DPP4 inhibitor and sweetener and for the case of dosing with each substance alone in accordance with the method described in (1) above.

C57BL/6J mice were used for the study animals.

10 mg/kg of (2S)-2-cyano-1-[trans-4-(dimethylaminocarbonyl)cyclohexylamino]acetylpyrrolidine hydrochloride (hereinafter referred to as Compound A) was orally administered (10 mL/kg) as DPP4 inhibitor. Purified water was orally administered as a control (10 mL/kg).

In addition, 6 g/kg of fructooligosaccharide (Meiji Seika Kaisha Ltd.) was used for the sweetener and administered orally (10 mL/kg). Purified water was administered as a control (10 mL/kg).

As a result, in the group dosed with both Compound A (10 mg/kg) and fructooligosaccharide (6 g/kg), levels of active GLP-1 in plasma demonstrated significantly higher values in comparison with the control group at each of 30, 60, 180 and 300 minutes after dosing, which demonstrates that the levels of active GLP-1 in plasma are maintained at a higher level continuously. On the other hand, in the groups dosed with Compound A (10 mg/kg) alone or fructooligosaccharide (6 g/kg) alone, there were no increases in plasma active GLP-1 levels observed. The results are shown in FIG. 2.

In addition, a similar test was carried out using xylose for the test sweetener orally administered at 6 g/kg in combination with Compound A (10 mg/kg). As a result, in the group administered xylose in combination with Compound A, remarkable increases in plasma active GLP-1 levels were observed as compared with the control group.

Example 3

Body Weight-Reducing Effect by Combined Use of DPP4 Inhibitor and Sweetener (1)

(1) Test Method:

[Body Weight-Reducing Test Using DIO (Diet-Induced Obesity) Mice]:

High fat diet-fed, male C57BL/6J mice (Clea Japan, Inc.) were used in the test.

Fed a high fat diet was carried out by allowing 3-week-old, male C57BL/6J mice (Clea Japan, Inc.) to free access to a high-fat diet having 37.2 w/w % fat content and 5.578 kcal/g calorie level (available from Oriental Yeast Co., Ltd.) for feed. Normal diet control mice were allowed free access to CRF-1 (fat content: 5.7 w/w %, calorie level: 3.59 kcal/g, available from Oriental Yeast Co., Ltd.).

The mice were used in the test after housing to age 39 weeks while fed a high fat diet in this manner.

These study animals were used in the test after first grouping according to body weight and blood sugar level.

The animals were administered test DPP4 inhibitor and test sweetener either orally or in-feed.

In the case of oral administration, the test substances [solutions of the test DPP4 inhibitor (or purified water as a control) and test sweetener (or purified water as a control)] were orally administered at 10 mL/kg twice a day and administered repeatedly for up to 2 weeks.

In the case of in-feed administration, the test substances (test DPP4 inhibitor and test sweetener) were finely ground with an agate mortar and added to feed (high fat diet, available from Oriental Yeast Co., Ltd.) and administered in this manner for up to 2 weeks.

Body weight and food intake were measured over time after the start of administration of the test substances.

Moreover, in the case body weight-reducing effect was observed, body composition was measured using a laboratory mouse X-ray body fat percentage measuring device (PIXImus2, GE Medical Systems Inc.) under pentobarbital anesthesia (70 mg/kg, i.p.).

Measurement results were tested for the presence of a significant difference between groups by comparing the sweetener-loaded groups with the control group using Dunnett's multiple comparison test (two-sided test). Here, a P value less than 5% was considered statistically significant, and statistical analysis software (EXSAS: Biological Experimental Data Statistical Analysis System, Arm Systex Co., Ltd.) was used to analyze the data.

(2) Test Results:

Body weight-reducing effect was tested for the cases of combined use of DPP4 inhibitor and sweetener and for the cases of dosing with each substance alone in accordance with the method described in (1) above.

(2S)-2-cyano-1-[trans-4-(dimethylaminocarbonyl)cyclohexylamino]acetylpyrrolidine hydrochloride (hereafter referred to as Compound A) as DPP4 inhibitor was administered in-feed at 10 mg/100 g.

In addition, fructooligosaccharide (Meiji Seika Kaisha Ltd.) for the sweetener was administered in-feed at 10 w/w %.

As a result, in the group dosed with both Compound A (10 mg/100 g) and fructooligosaccharide (10 w/w %), body weights decreased significantly and body weight reducing effect was observed in comparison with the control group at 2 to 14 days after dosing. On the other hand, there were no changes in body weight in the group dosed with Compound A alone (10 mg/100 g) as compared with the control group. In addition, in the group dosed with fructooligosaccharide alone (10 w/w %), although body weights tended to decrease somewhat, there were no significant differences observed in comparison with the control group. The results are shown in FIG. 3.

In addition, as a result of measuring body composition at 15 days after dosing, in the group dosed with both Compound A (10 mg/100 g) and fructooligosaccharide (10 w/w %), there was no change in lean mass (g) in comparison with the control group, while only fat mass (g) decreased significantly as compared with the control group. On the basis thereof, it was thought that administration of both Compound A and fructooligosaccharide allowed the obtaining of body fat mass reducing effect.

Example 4

GLP-1 Secretion-Stimulating Action by Combined Use of DPP4 Inhibitor and Sweetener (Blood Active GLP-1 Level-Increasing Action) (2)

(1) Test Method:

Male C57BL/6J mice (Clea Japan, Inc.) (7-week-old at time of use) were used in the test.

These study animals were used in the test after first fasting starting on the night prior to the test and then grouping according to body weight. The animals were orally administered test DPP4 inhibitor (or purified water as a control) (10 mL/kg). At 30 minutes after administration, the animals were then orally administered (10 mL/kg) a solution of test sweetener (or purified water as a control) followed by collecting blood samples at 0, 30, 60, 180 and 300 minutes after administration. These samples were then measured for concentrations of active GLP-1 in plasma.

Measurement of plasma active GLP-1 concentrations and analysis and testing of the measurement results were carried out in the same manner as (1) of Example 1 above.

(2) Test Results:

Fructooligosaccharide (Meiji Seika Kaisha Ltd.), kestose (Meiji Seika Kaisha Ltd., GF2), raffinose (Wako Pure Chemical Industries, Ltd.), melibiose (Wako Pure Chemical Industries, Ltd.), xylooligosaccharide (Suntory Ltd.), xylose (Wako Pure Chemical Industries, Ltd.), xylitol (Wako Pure Chemical Industries, Ltd.), sorbitol (Wako Pure Chemical Industries, Ltd.), D-mannitol (Wako Pure Chemical Industries, Ltd.), erythritol (Wako Pure Chemical Industries, Ltd.), maltitol (Hayashibara Biochemical Laboratories, Inc.), sucralose (San-Ei Gen F.F.I., Inc.) or acesulfame K (Wako Pure Chemical Industries, Ltd.) was used as sweetener and administered orally (10 mL/kg) at 6 g/kg, 3 g/kg or 1 g/kg.

In addition, (2S)-2-cyano-1-[trans-4-(dimethylaminocarbonyl)cyclohexylamino]acetylpyrrolidine benzenesulfonate (hereafter referred to as Compound A') as DPP4 inhibitor (or purified water as a control) was used at 10 mg/kg and administered orally (10 mL/kg).

Blood active GLP-1 level-increasing action was tested for the cases of combined use of DPP4 inhibitor and each type of sweetener in accordance with the method described in (1) above (n=4 to 5 animals per group).

The results are shown in Table 1. Blood active GLP-1 concentrations (1 hour after dosing) in the groups dosed with both each type of sweetener (6 g/kg, 3 g/kg or 1 g/kg) and Compound A' (10 mg/kg) were represented as relative values with respect to blood active GLP-1 concentrations (1 hour after dosing) in the group dosed with fructooligosaccharide (6 g/kg) and Compound A'.

In each of the groups dosed with each sweetener shown in Table 1 (6 g/kg, 3 g/kg or 1 g/kg) and Compound A', increases in levels of active GLP-1 were observed, and those increases were observed to be equal to or greater than increases observed in the group dosed with fructooligosaccharide (6 g/kg) and Compound A' (10 mg/kg).

TABLE 1

| DPP4 Inhibitor | Sweetener | Plasma active GLP-1 concentration (relative value(*)) |
|---|---|---|
| Compound A' (10 mg/kg) | Fructooligosaccharide (6 g/kg) | 100 |
| | Kestose (6 g/kg) = GF2 | 166 |
| | Raffinose (6 g/kg) | 77 |
| | Melibiose (6 g/kg) | 454 |
| | Xylooligosaccharide (6 g/kg) | 178 |
| | Xylose (6 g/kg) | 597 |
| | Xylitol (3 g/kg) | 272 |
| | (6 g/kg) | 774 |
| | Sorbitol (3 g/kg) | 286 |
| | (6 g/kg) | 863 |

TABLE 1-continued

| DPP4 Inhibitor | Sweetener | Plasma active GLP-1 concentration (relative value(*)) |
|---|---|---|
| | D-mannitol (3 g/kg) | 160 |
| | (6 g/kg) | 742 |
| | Erythritol (3 g/kg) | 147 |
| | (6 g/kg) | 461 |
| | Maltitol (6 g/kg) | 422 |
| | Sucralose (6 g/kg) | 166 |
| | Acesulfame K (1 g/kg) | 149 |
| | (3 g/kg) | 377 |

*Relative value based on a value of 100 for plasma active GLP-1 concentration (1 hour after dosing) obtained by administration of Compound A' and fructooligosaccharide (6 g/kg)

Example 5

GLP-1 Secretion-Stimulating Action by Combined Use of DPP4 Inhibitor and Sweetener (Blood Active GLP-1 Level-Increasing Action) (3)

(1) Test Method:

Testing was carried out in the same manner as (1) of Example 4 above. Measurement of plasma active GLP-1 concentrations and analysis and testing of the measurement results were carried out in the same manner as (1) of Example 1 above.

(2) Test Results:

Sitagliptin (MK-0413) at 10 mg/kg, alogliptin (SYR-322) at 1 mg/kg, vildagliptin (LAF237) at 10 mg/kg, saxagliptin (BMS-477118) at 3 mg/kg, Compound A' at 10 mg/kg or Compound B ((2S)-2-cyano-1-[t-4-(4-propionyl-1-piperazinyl)-1-methyl-r-1-cyclohexylamino]acetyl pyrrolidine) at 10 mg/kg was used as DPP4 inhibitor and administered orally (10 mL/kg). Purified water was administered orally (10 mL/kg) as a control.

D-mannitol (Wako Pure Chemical Industries, Ltd.) at 3 g/kg, melibiose (Wako Pure Chemical Industries, Ltd.) at 6 g/kg or acesulfame K (Wako Pure Chemical Industries, Ltd.) at 3 g/kg was used as sweetener and administered orally (10 mL/kg). Purified water was administered orally (10 mL/kg) as a control.

Blood active GLP-1 level-increasing action was tested for the cases of combined use of each type of DPP4 inhibitor and each type of sweetener in accordance with the method described in (1) above (n=5 animals per group).

Figure 4A:
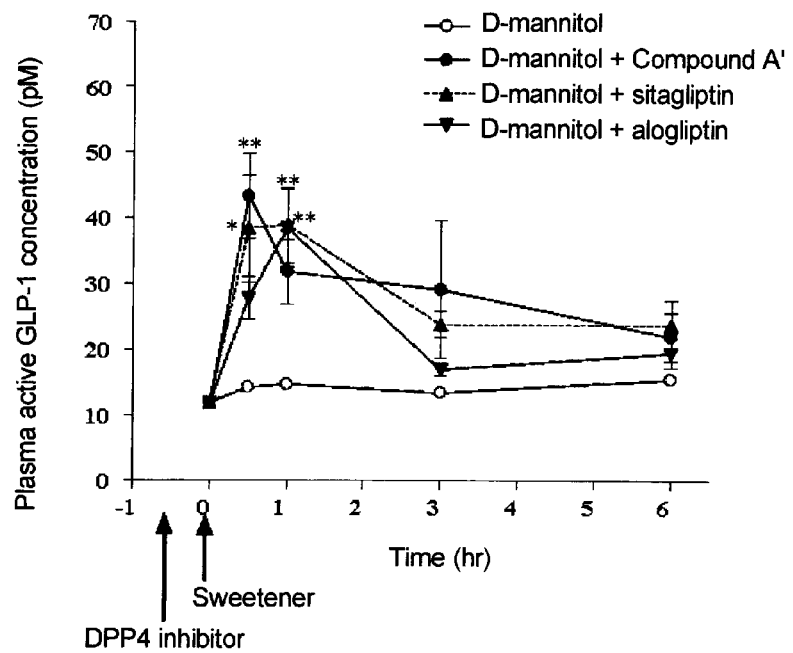
FIG. 4a shows the test results for action in increasing plasma active GLP-1 level in the case of having administered D-mannitol and DPP4 inhibitor (Compound A', Sitagliptin or Alogliptin) to C57BL/6J mice. White circles (○) indicate time-dependent changes in plasma active GLP-1 concentration (mean±standard error (SEM))) in a group orally administered 3 g/kg of D-mannitol alone, black circles (●) indicate the same time-dependent changes in a group orally administered 3 g/kg of D-mannitol and 10 mg/kg of DPP4 inhibitor (Compound A'), black triangles (▲) indicate the same time-dependent changes in a group orally administered 3 g/kg of D-mannitol and 10 mg/kg of DPP4 inhibitor (Sitagliptin), and inverted black triangles (▼) indicate the same time-dependent changes in a group orally administered 3 g/kg of D-mannitol and 10 mg/kg of DPP4 inhibitor (Alogliptin) (n=5 for all groups). (*: $p<0.05$, **: $p<0.01$: significant differences versus control group based on Dunnett's multiple comparison method.)
Figure 4B:
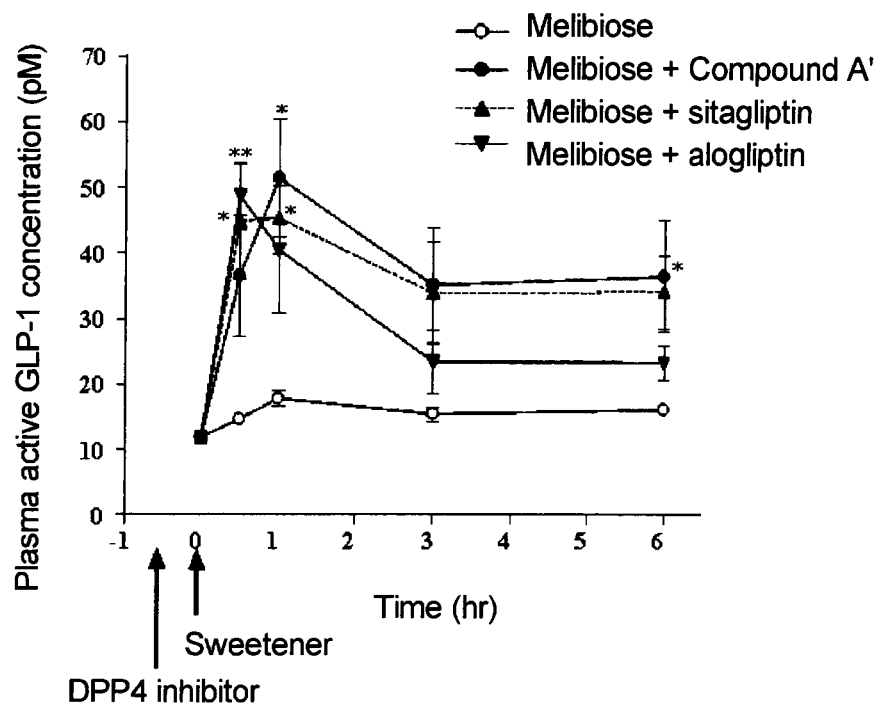
FIG. 4b shows the test results for action in increasing plasma active GLP-1 level in the case of having administered melibiose and DPP4 inhibitor (Compound A', Sitagliptin or Alogliptin) to C57BL/6J mice. White circles (○) indicate time-dependent changes in plasma active GLP-1 concentration (mean±standard error (SEM)) in a group orally administered 6 g/kg of melibiose alone, black circles (●) indicate the same time-dependent changes in a group orally administered 6 g/kg of melibiose and 10 mg/kg of DPP4 inhibitor (Compound A'), black triangles (▲) indicate the same time-dependent changes in a group orally administered 6 g/kg of melibiose and 10 mg/kg of DPP4 inhibitor (Sitagliptin), and inverted black triangles (▼) indicate the same time-dependent changes in a group orally administered 6 g/kg of melibiose and 10 mg/kg of DPP4 inhibitor (Alogliptin) (n=5 for all groups). (*: $p<0.05$, **: $p<0.01$: significant differences versus control group based on Dunnett's multiple comparison method.)
Figure 4C:
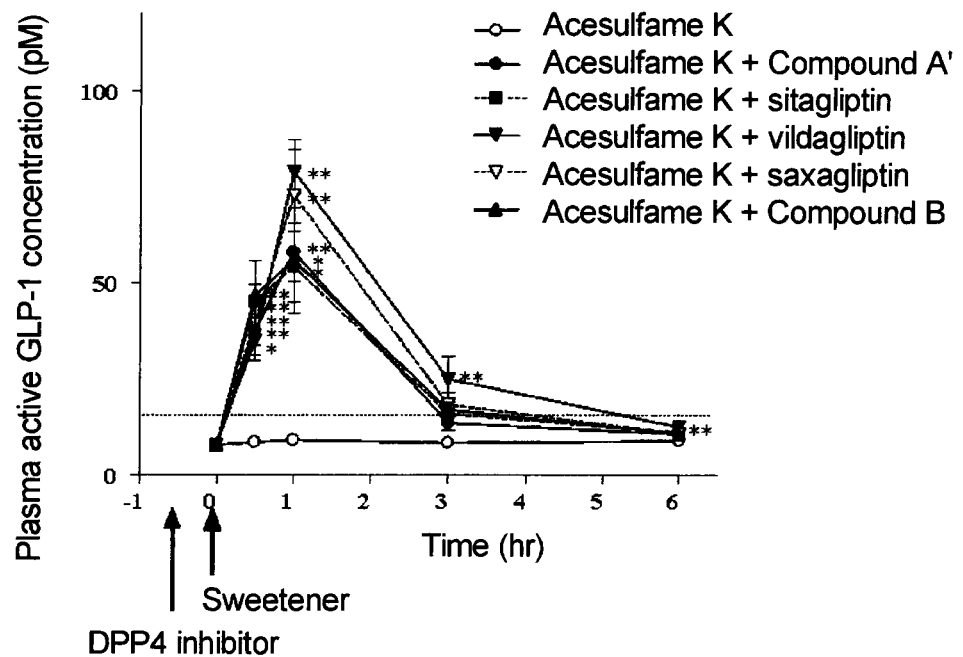
FIG. 4c shows the test results for action in increasing plasma active GLP-1 level in the case of having administered acesulfame K and DPP4 inhibitor (Compound A', Sitagliptin, Vildagliptin, Saxagliptin or Compound B) to C57BL/6J mice. White circles (○) indicate time-dependent changes in plasma active GLP-1 concentration (mean±standard error (SEM)) in a group orally administered 3 g/kg of acesulfame K alone, black circles (●) indicate the same time-dependent changes in a group orally administered 3 g/kg of acesulfame K and 10 mg/kg of DPP4 inhibitor (Compound A'), black squares (■) indicate the same time-dependent changes in a group orally administered 3 g/kg of acesulfame K and 10 mg/kg of DPP4 inhibitor (Sitagliptin), inverted black triangles (▼) indicate the same time-dependent changes in a group orally administered 3 g/kg of acesulfame K and 10 mg/kg of DPP4 inhibitor (Vildagliptin), inverted white triangles (∇) indicate the same time-dependent changes in a group orally administered 3 g/kg of acesulfame K and 10 mg/kg of DPP4 inhibitor (Saxagliptin), and black triangles (▲) indicate the same time-dependent changes in a group orally administered 3 g/kg of acesulfame K and 10 mg/kg of DPP4 inhibitor (Compound B) (n=5 for all groups). (*: $p<0.05$, **: $p<0.01$: significant differences versus control group based on Dunnett's multiple comparison method.)

The results are shown in FIGS. 4a, 4b and 4c and in Table 2.

As shown in FIGS. 4a, 4b and 4c, the levels of plasma active GLP-1 in the groups dosed with each type of sweetener and each type of DPP4 inhibitor demonstrated higher values as compared with the control groups (groups dosed with each sweetener alone) at each of 30, 60, 180 and 360 minutes after dosing.

In addition, as shown in Table 2, increases in levels of plasma active GLP-1 (increases in AUC) in the groups dosed with each type of sweetener and each DPP4 inhibitor demonstrated significantly higher values as compared with the control groups (groups dosed with each sweetener alone or group dosed with DPP4 inhibitor alone).

TABLE 2

| Sweetener | DPP4 inhibitor | Increase in AUC of Plasma active GLP-1 (pM · Hr)[a] |
|---|---|---|
| (purified water) | Sitagliptin (MK-0413) (10 mg/kg) | 79 ± 1 |
| D-mannitol | (purified water) | 85 ± 1 |

TABLE 2-continued

| Sweetener | DPP4 inhibitor | Increase in AUC of Plasma active GLP-1 (pM · Hr)[a] |
|---|---|---|
| (3 g/kg) | Sitagliptin (MK-0413) (10 mg/kg) | 166 ± 9 ** |
| | Alogliptin (SYR-322) (1 mg/kg) | 136 ± 7 |
| | Compound A' (10 mg/kg) | 170 ± 27 ** |
| Melibiose (6 g/kg) | (purified water) | 95 ± 2 |
| | Sitagliptin (MK-0413) (10 mg/kg) | 218 ± 18 ** |
| | Alogliptin (SYR-322) (1 mg/kg) | 172 ± 10 * |
| | Compound A' (10 mg/kg) | 228 ± 32 ** |
| Acesulfame K (3 g/kg) | (purified water) | 51 ± 1 |
| | Sitagliptin (MK-0413) (10 mg/kg) | 148 ± 13 ** |
| | Vildagliptin (LAF237) (10 mg/kg) | 199 ± 18 ** |
| | Saxagliptin (BMS-477118) (3 mg/kg) | 174 ± 10 ** |
| | Compound A' (10 mg/kg) | 142 ± 11 ** |
| | Compound B (10 mg/kg) | 153 ± 14 ** |

[a] Mean ± standard error (SEM), n = 5,
* $p < 0.05$,
** $p < 0.01$ (significant differences versus control group based on Dunnett's multiple comparison method)

Example 6

Body Weight-Reducing Effect by Combined Use of DPP4 Inhibitor and Sweetener (2)

(1) Test Method:
[Body Weight-Reducing Test Using DIO (Diet-Induced Obesity) Mice]:
Testing was carried out in the same manner as (1) of Example 3 above. High fat diet-fed, male C57BL/6J mice housed until age 14 to 22 weeks were used in the test.

The study animals were used in the test after first grouping according to body weight and blood sugar level.

The animals were administered test DPP4 inhibitor and test sweetener in-feed for up to 15 days.

Body weights and food intake were measured over time after the start of administration of the test substances. Testing and analysis of measurement results were carried out in the same manner as (1) of Example 3 above.

In addition, in the case body weight reducing effect was observed, body composition was measured in the same manner as (1) of Example 3 above.

(2) Test Results:
D-mannitol (Wako Pure Chemical Industries, Ltd.), melibiose (Wako Pure Chemical Industries, Ltd.) or acesulfame K (Wako Pure Chemical Industries, Ltd.) was used as sweetener and each was administered in-feed at 5 w/w %. In addition, Compound A' was administered as DPP4 inhibitor in-feed at 10 mg/100 g.

Body weight reducing-effect was tested for the cases of combined use of each of these sweeteners and DPP4 inhibitor in accordance with the method described in (1) above (n=9 animals per group).

Figure 5A:
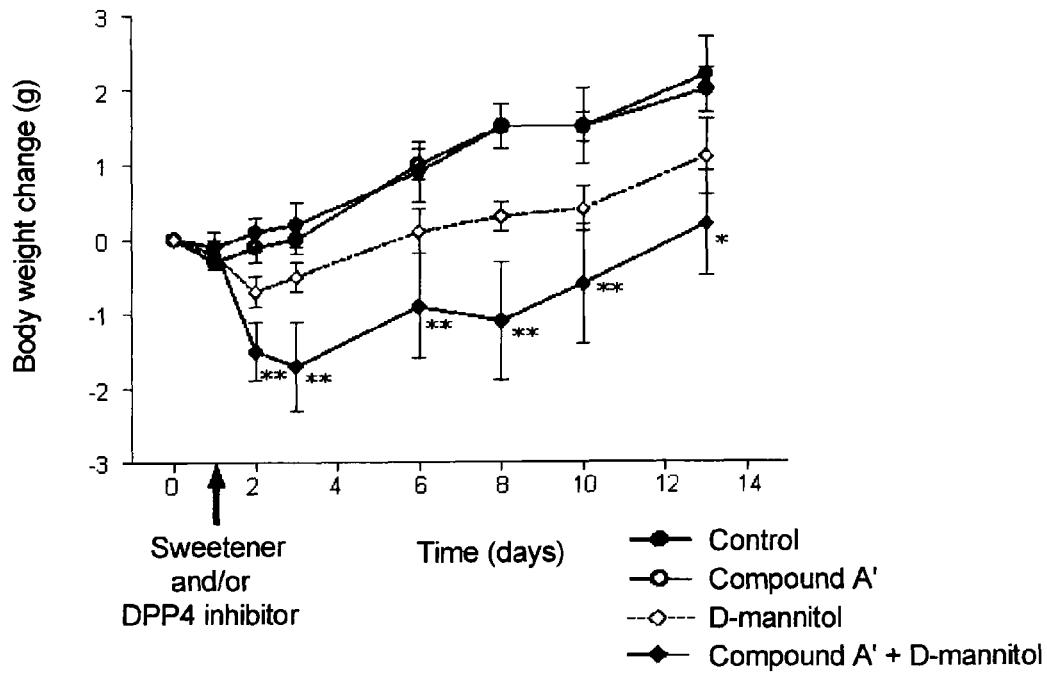
FIG. 5a shows the test results for action in reducing body weight in the case of in-feed administration of DPP4 inhibitor (Compound A') and D-mannitol to high fat diet-fed C57BL/6J mice. Black circles (●) indicate daily changes in body weight (mean±standard error (SEM))) in a group of mice only fed a high fat diet as a control, white circles (○) indicate the same daily changes in a group of high fat diet-fed mice administered in-feed 10 mg/100 g of DPP4 inhibitor (Compound A') alone, white diamonds (◇) indicate the same daily changes in a group of high fat diet-fed mice orally administered 5 w/w % of D-mannitol alone, and black diamonds (◆) indicate the same daily changes in a group of high fat diet-fed mice administered in-feed both 10 mg/100 g DPP4 inhibitor (Compound A') and 5 w/w % of D-mannitol (n=9 for all groups). (*: $p<0.05$, **: $p<0.01$: significant differences versus control group based on Dunnett's multiple comparison method.)
Figure 5B:
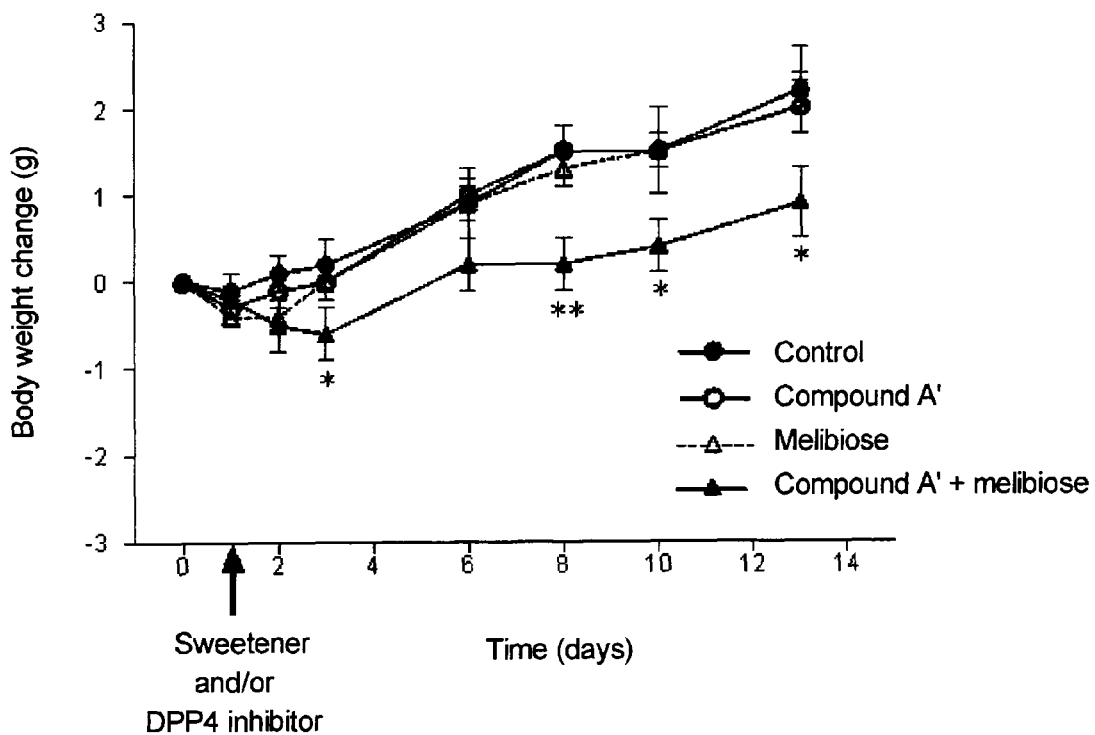
FIG. 5b shows the test results for action in reducing body weight in the case of in-feed administration of DPP4 inhibitor (Compound A') and melibiose to high fat diet-fed C57BL/6J mice. Black circles (●) indicate daily changes in body weight (mean±standard error (SEM))) in a group of mice only fed a high fat diet as a control, white circles (○) indicate the same daily changes in a group of high fat diet-fed mice administered in-feed 10 mg/100 g of DPP4 inhibitor (Compound A') alone, white triangles (Δ) indicate the same daily changes in a group of high fat diet-fed mice orally administered 5 w/w % of melibiose alone, and black triangles (▲) indicate the same daily changes in a group of high fat diet-fed mice administered in-feed both 10 mg/100 g of DPP4 inhibitor (Compound A') and 5 w/w % of melibiose (n=9 for all groups). (*: $p<0.05$, **: $p<0.01$: significant differences versus control group based on Dunnett's multiple comparison method.)
Figure 5C:
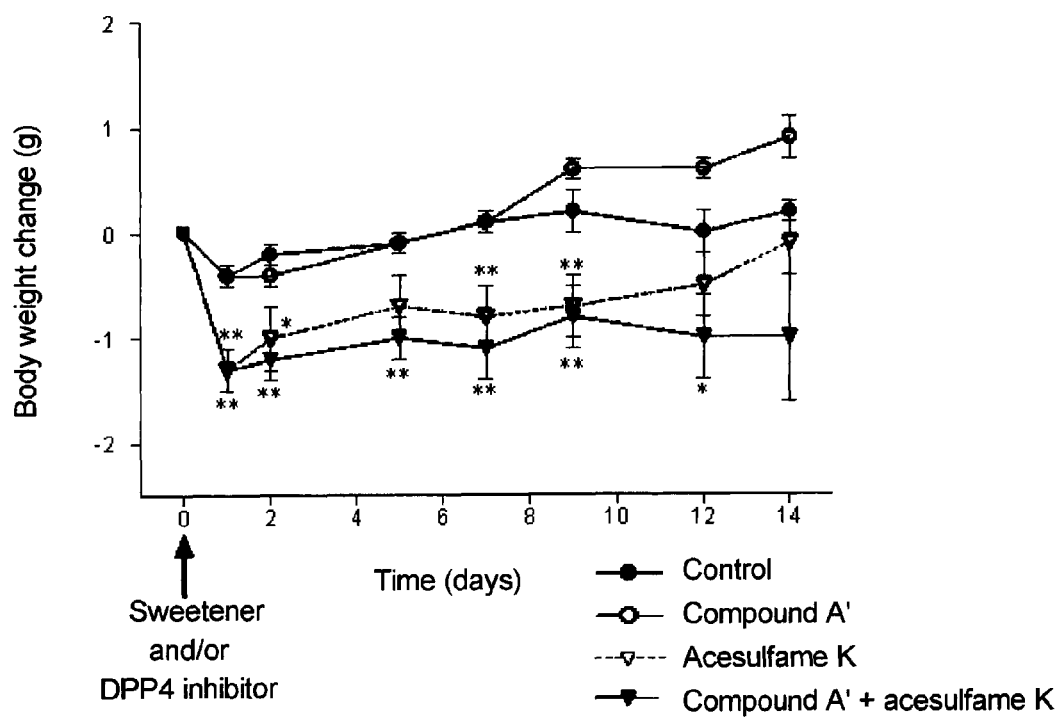
FIG. 5c shows the test results for action in reducing body weight in the case of in-feed administration of DPP4 inhibitor (Compound A') and acesulfame K to high fat diet-fed C57BL/6J mice. Black circles (●) indicate daily changes in body weight (mean±standard error (SEM))) in a group of mice only fed a high fat diet as a control, white circles (○) indicate the same daily changes in a group of high fat diet-fed mice administered in-feed 10 mg/100 g of DPP4 inhibitor (Compound A') alone, inverted white triangles (∇) indicate the same daily changes in a group of high fat diet-fed mice orally administered 5 w/w % of acesulfame K alone, and inverted black triangles (▼) indicate the same daily changes in a group of high fat diet-fed mice administered in-feed both 10 mg/100 g of DPP4 inhibitor (Compound A') and 5 w/w % of acesulfame K (n=9 for all groups). (*: $p<0.05$, **: $p<0.01$: significant difference versus control group based on Dunnett's multiple comparison method.)

The results are shown in FIGS. 5a, 5b and 5c and in Tables 3-a, 3-b and 3-c.

As shown in FIGS. 5a, 5b and 5c, in the groups dosed with both DPP4 inhibitor and each sweetener (D-mannitol, melibiose or acesulfame K), body weights significantly decreased as compared with the control group on each of days 2 to 13 (or day 12) after dosing, and body weight-reducing effect was observed.

On the other hand, there were no changes in body weight as compared with the control group in the group dosed with Compound A' alone.

In addition, there were no significant differences as compared with the control group in the groups dosed with only each type of sweetener (D-mannitol, melibiose or acesulfame K).

The data obtained at 13 days (or 12 days) after dosing is as shown in Tables 3(a), 3(b) and 3(c).

On the basis of these results, synergistic body weight reducing effects were thought to be obtained by combined use of each type of sweetener (D-mannitol, melibiose or acesulfame K) and DPP4 inhibitor.

TABLE 3-a

| Sweetener | DPP4 inhibitor | Body weight gain after 13 days (g)[a] |
|---|---|---|
| — | — | 2.2 ± 0.5 |
| — | Compound A' (administered in feed at 10 mg/100 g) | 2.0 ± 0.3 |
| D-mannitol (administered in feed at 5 w/w %) | — | 1.1 ± 0.5 |
| D-mannitol (administered in feed at 5 w/w %) | Compound A' (administered in feed at 10 mg/100 g) | 0.2 ± 0.7 * |

[a] Mean ± standard error (SEM), n = 9,
* $p < 0.05$,
** $p < 0.01$ (significant differences versus control group based on Dunnett's multiple comparison method)

TABLE 3-b

| Sweetener | DPP4 inhibitor | Body weight gain after 13 days (g)[a] |
|---|---|---|
| — | — | 2.2 ± 0.5 |
| — | Compound A' (administered in feed at 10 mg/100 g) | 2.0 ± 0.3 |
| Melibiose (administered in feed at 5 w/w %) | — | 2.2 ± 0.2 |
| Melibiose (administered in feed at 5 w/w %) | Compound A' (administered in feed at 10 mg/100 g) | 0.9 ± 0.4 * |

[a] Mean ± standard error (SEM), n = 9,
* $p < 0.05$,
** $p < 0.01$ (significant differences versus control group based on Dunnett's multiple comparison method)

TABLE 3-c

| Sweetener | DPP4 inhibitor | Body weight gain after 12 days (g)[a] |
|---|---|---|
| — | — | 0.0 ± 0.2 |
| — | Compound A' (administered in feed at 10 mg/100 g) | 0.6 ± 0.1 |
| Acesulfame K (administered in feed at 5 w/w %) | — | −0.5 ± 0.3 |
| Acesulfame K (administered in feed at 5 w/w %) | Compound A' (administered in feed at 10 mg/100 g) | −1.0 ± 0.4 * |

[a]Mean ± standard error (SEM), n = 9,
* p < 0.05,
** p < 0.01 (significant differences versus control group based on Dunnett's multiple comparison method)

In addition, as a result of measuring body composition 15 days after dosing in the groups in which D-mannitol and acesulfame K were used as sweeteners, in the group dosed with both Compound A' and D-mannitol or the group dosed with both Compound A' and acesulfame K, there was no change in lean mass (g) in comparison with the control group, while only fat mass (g) decreased significantly as compared with the control group.

Example 7

Body Weight-Reducing Effect by Combined Use of DPP4 Inhibitor and Sweetener (3)

(1) Test Method:

[Body Weight-Reducing Effect Test Using DIO (Diet-Induced Obesity) Mice]:

Testing was carried out in the same manner as (1) of Example 3 above. High fat diet-fed, male C57BL/6J mice housed until age 16 weeks were used in the test.

The study animals were used in the test after first grouping according to body weight.

The animals were administered test DPP4 inhibitor and test sweetener in-feed for up to 15 days. Body weights and food intake were measured over time after the start of administration of the test substances.

(2) Test Results:

Sorbitol (Wako Pure Chemical Industries, Ltd.) or erythritol (Wako Pure Chemical Industries, Ltd.) was used as sweetener and each was administered in-feed at 5 w/w %. In addition, Compound A' was administered as DPP4 inhibitor in-feed at 10 mg/100 g. Body weight reducing effect was tested for the cases of combined use of each of these sweeteners and DPP4 inhibitor in accordance with the method described in (1) above (n=7 animals per group).

The results are shown in Table 4.

As shown in Table 4, in the groups dosed with both DPP4 inhibitor and each of the sweeteners (sorbitol or erythritol), decreases in body weights were observed as compared with the control group.

Furthermore, decreases in body weights were not observed as compared with the control group in separate tests involving the case of administering each sweetener (sorbitol or erythritol) alone.

TABLE 4

| Sweetener | DPP4 inhibitor | Body weight gain (g)[a] | |
|---|---|---|---|
| | | After 8 days | After 15 days |
| — | — | 0.8 ± 0.3 | 1.9 ± 0.3 |
| Sorbitol (administered in feed at 5 w/w %) | Compound A' (administered in feed at 10 mg/100 g) | −0.7 ± 0.4 * | 0.8 ± 0.3 |
| Erythritol (administered in feed at 5 w/w %) | Compound A' (administered in feed at 10 mg/100 g) | 0.2 ± 0.1 | 0.9 ± 0.3 |

[a]Mean ± standard error (SEM), n = 7,
* p < 0.05,
** p < 0.01 (significant differences versus control group based on Dunnett's multiple comparison method)

INDUSTRIAL APPLICABILITY

The pharmaceutical composition, therapeutic or preventive method or use thereof according to the present invention is useful for reducing body weight and/or reducing body fat mass in patients suffering from symptoms of obesity, and is also useful for the treatment or prevention of obesity.

The invention claimed is:

1. A method for reducing body weight or reducing body fat mass of a patient suffering from symptoms of obesity, comprising administering an effective amount of (a) at least one dipeptidyl peptidase 4 inhibitor and (b) at least one sweetener having a GLP-1 secretion-stimulating action to the patient suffering from symptoms of obesity; wherein the at least one sweetener having a GLP-1 secretion-stimulating action is
    a non-saccharide sweetener chosen from acesulfame K, sucralose, aspartame, and stevia.

2. The method according to claim 1, wherein the at least one sweetener having a GLP-1secretion-stimulating action is chosen from acesulfame K and sucralose.

3. The method according to claim 1, wherein the at least one sweetener having a GLP-1 secretion-stimulating action is acesulfame K.

4. The method according to claim 1, 2, or 3, wherein administration of (a) is carried out simultaneous to administration of (b), before administration of (b), or after administration of (b).

5. The method according to claim 1, 2, or 3, wherein the patient suffering from symptoms of obesity is suffering from type 2 diabetes in combination.

6. The method according to claim 1, 2, or 3, wherein the at least one dipeptidyl peptidase 4 inhibitor is chosen from:
   (2S)-2-cyano-1-[trans-4-(dimethylaminocarbonyl) cyclohexylamino]acetylpyrrolidine;
   (2S)-2-cyano-1-[trans-4-(morpholinocarbonyl) cyclohexylamino]acetylpyrroidine;
   (2S)-2-cyano-1-[trans-4-(4-acetyl piperazin-1-yl-carbonyl)cyclohexylaminoj acetylpyrrolidine;
   (2S)-2-cyano-1-[t-4-acetyl-1-piperazinyl)-1-methyl-r-1-cyclohexylaminojacetylpyrrolldlne;
   (2S)-2-cyano-1-[t-4-(4-propionyl-1-piperazinyl)-1-methyl-r-1-cyclohexylaminojacetylpyrrolidine;
   3-{(2S, 4S)-4- [4-(3-methyl-1-phenyl-1H-pyrazol-5-yl) piperazin-1-yl] pyrrolidin-2-ylcarbonyl}thiazolidine;
   (3R)-3-amino-1-[9-(trifluoromethyl)-1, 4, 7, 8-tetraazabicyclo[4.3.0]nona-6,8-dien-4-yl]-4-(2,4,5-triftuorophenyl)butan-1-one;
   (2S)-1-[2-[(3-hydroxy-1-adamantyl)amino]acetyl]pyrrolidine-2-carbonitrile;
   (1S, 3S, 5S)-2-[(2S)-2-amino-2-(3-hydroxy-1-adamantyl) acetyl]-2-azabicyclo[3-1-0]hexane-3-carbonitrile;

6-[(3R)-3-aminopiperidin-1-yl]-1-(2-cyanobenzyl)-3-methylpyrimidin-2, 4(1H, 3H)-dione;
L-threo-isoleucyl pyrrolidide;
L-allo-isoleucyl thiazolidide; and
L-allo-isoleucyl pyrrolidide; or pharmaceutically acceptable salts thereof.

7. The method according to claim 1, 2, or 3, wherein the at least one dipeptidyl peptidase 4 inhibitor s chosen from:
(2S)-2-cyano-1-[trans-4-(dimethylaminocarbonyl) cyclohexylaino]acetylpyrrolidine;
(2S)-2-cyano-1-[trans-4-(morpholinocarbonyl) cyclohexylamino]acetylpyrrolidine;
(2S)-2-cyano-1-[trans-4-(4-acetyl piperazin-1-yl-carbonyl)cyclohexylamino]acetylpyrrolidine;
(2S)- 2-cyano-1-[t-4-(4-acetyl-1-piperazinyl)- 1-methyl-r-1-cyclohexylamino]acetylpyrrolidine;
(2S)- 2-cyano-1-[t-4-(4-propionyl-1-piperazinyl)-1-methyl-r-1-cyclohexylamino]acetyl pyrrolidine;
3-{2S, 4S)-4-[4-(3-methyl-1-phenyl-1 H-pyrazol-5-yl) piperazin-1-yl]pyrrolidin-2-ylcarbonyl}thiazolidine;
(3R)-3-amino-1-[9-(trifluoromethyl)-1,4,7, 8-tetraazabicyclo[4.3.0]nona-6,8-dien-4-yl)-4-(2, 4, 5-trifluorophenyl)butan-1-one;
(2S)-1-[2[(3-hydroxy-1-adamantyl)amino]acetyl]pyrrolidine-2-carbonitrile;
(1S, 3S, 5S)-2-[(2S)2-amino-2-(3-hydroxy-1-adamantyl) acetyl]-2-azabicyclo[3.1.0]hexane-3-carbonitrile; and
6-[(3R)-3-aminopiperidin-1-yl]-1-(2 -cyanobenzyl)-3-methylpyrimidin-2,4(1 H,3H)-dione;
or pharmaceutically acceptable salts thereof.

8. The method according to claims 2 or 3, wherein the at least one dipeptidyl peptidase 4 inhibitor is chosen from:
(2S)-2-cyano-1-[trans-4-(dimethylaminocarbonyl) cyclohexylamino]acetylpyrrolidine;
(2S)-2-cyano-1-[t-4-(4-propionyl-1-piperazinyl)-1-methyl-r-1-cyclohexylamino]acetylpyrrolidine;
3-{(2S, 4S)-4-[4-(3-methyl-1-phenyl-1 H-pyrazol-5-yl) piperazin-1-yl] pyrrolidin-2-ylcarbonyl}thiazolidine;
(3R)-3-amino-1-[9-(trifluoromethyl)-1,4,7,8-tetraazabicyclo[4.3.0]nona-6,8-dien-4-y]-4-(2-4,5-trifluorophenyl)butan-1-one;
(2S)-1-[2-[(3-hydroxy-1-adamantyl)amino]acetyl)pyrrolidine-2-carbonitrile;
(1S, 3S, 5S)-2-[(2S)-2-amino-2-(3-hydroxy-1-adamantyl) acetyl]-2-azabicyclo[3.1.0]hexane,-3-carbonitrile; and
6-[(3R)-3-aminopiperidin-1-yl]-1-(2cyanobenzyl)3methylpyrimidin-2,4(1H, 3H)-dione;
or pharmaceutically acceptable salts thereof.

\* \* \* \* \*